(12) United States Patent
Lesage

(10) Patent No.: US 9,458,035 B1
(45) Date of Patent: Oct. 4, 2016

(54) METHOD OF NEUTRALIZING BACTERIA IN SULPHUR-CONTAINING HARD WATER IN A WATER HEATER

(71) Applicant: MICLAU-S.R.I. INC., Montreal East (CA)

(72) Inventor: Claude Lesage, Pointe-Claire (CA)

(73) Assignee: MICLAU-S.R.I. INC.

( * ) Notice: Subject to any disclaimer, the term of this patent is extended or adjusted under 35 U.S.C. 154(b) by 0 days.

(21) Appl. No.: 14/756,620

(22) Filed: Sep. 28, 2015

(51) Int. Cl.
- *C02F 1/46* (2006.01)
- *C02F 1/461* (2006.01)
- *A01N 59/16* (2006.01)
- *C02F 1/467* (2006.01)
- *C23F 13/14* (2006.01)

(52) U.S. Cl.
CPC ........... *C02F 1/46109* (2013.01); *A01N 59/16* (2013.01); *C02F 1/4672* (2013.01); *C23F 13/14* (2013.01); *C02F 2001/46133* (2013.01); *C02F 2201/461* (2013.01); *C02F 2303/02* (2013.01); *C02F 2303/04* (2013.01)

(58) Field of Classification Search
None
See application file for complete search history.

(56) References Cited

PUBLICATIONS

SteveJenkins.com, "How to fix Rotton Egg Smell in Your Water", Feb. 2015, pp. 1-18.*

* cited by examiner

*Primary Examiner* — Brian Gulledge
(74) *Attorney, Agent, or Firm* — Guy J. Houle; Houle Patent Agency Inc.

(57) ABSTRACT

A method of neutralizing odor-causing bacteria in sulphur-containing hard water in the tank of a water heater is described. The method comprises utilizing a 420 aluminum alloy sacrificial anode and introducing into the tank of the water heater zing, herein in pellet form, in the tank to prevent the formation of bad odor contained in the sulphur containing hard water by neutralizing the bad odor producing bacteria.

7 Claims, 1 Drawing Sheet

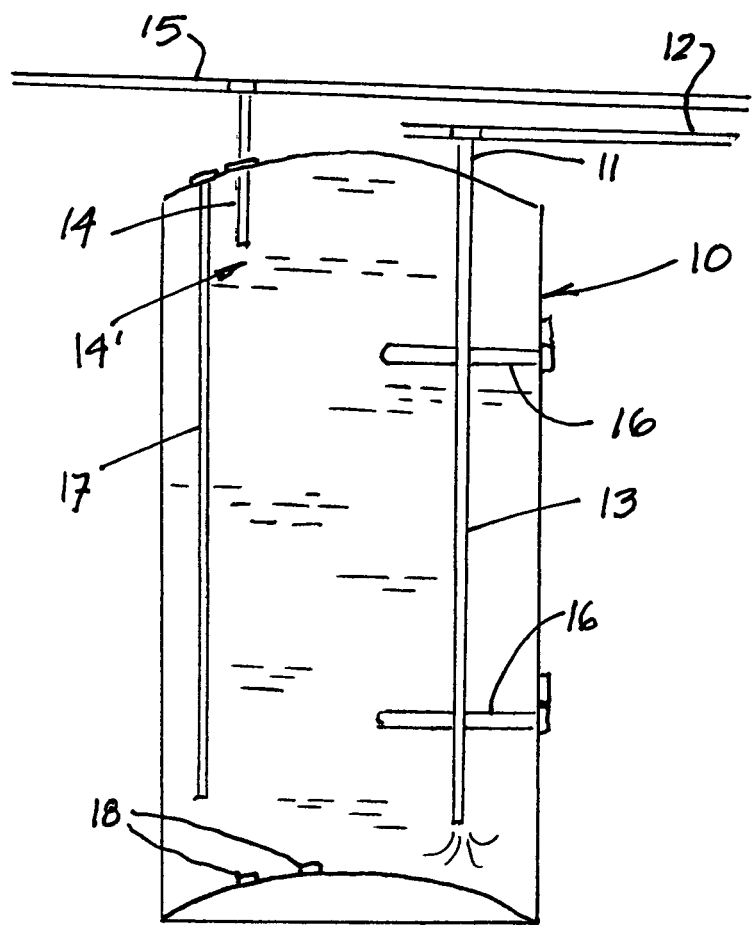

METHOD OF NEUTRALIZING BACTERIA IN SULPHUR-CONTAINING HARD WATER IN A WATER HEATER

FIELD OF INVENTION

The present invention relates to water heaters and more particularly to the neutralization of odor-causing bacteria in sulphur-containing hard water contained in such water heaters.

BACKGROUND OF THE INVENTION

Not all water supplies have the same quality water due to variations in its mineral composition. In certain regions water may produce bad odors, such as a rotten-egg smell due to certain types of bacterial produced by sulphur contained therein. Such water is known as hard water which emanates from underground where it is in contact with in all sorts of minerals. Such rotten-egg smell water when heated in a water heater is amplified. In an attempt to resolve this problem different aluminum sacrificial anode compositions have been developed wherein a certain percentage of zinc is introduced in the alloy. Sacrificial anodes are utilized in water heaters for cathodic corrosion protection of the cathode and which cathode consists of any exposed steel in a flawed glass-lined tank. The glass lining secured on the inside wall of the tank is to isolate the steel from the water and thereby increase the life span of the water heater. However, any flaws in the glass lining and about fittings exposes steel to the water and this causes electrolysis, a current flow, between the anode and the cathode and deterioration of the sacrificial anode. The intensity of the current flow amplifies the bad odor of the water.

In an attempt to protect the steel tank from corrosion and reduce the bad odors generated by such hard water, an aluminum-zinc alloy material was utilized as the anode for replacement of the commonly used magnesium anode. This offered some protection against certain bacteria contained in the water. The alloy composition contained zinc and trace metals, such as tin, iron and silicon and the balance aluminum. However, these replacement anodes, during electrolytic reaction, produced more hydrogen at the exposed steel surfaces than the magnesium anode when active. It was concluded that the higher production of hydrogen when combined with sulphur in hot water, accelerated the bad odors generated by the bacteria, particularly when the anode had been greatly consumed. Because such anode also deteriorated more quickly, there was a need for replacement after about four years of service which, of course, is dot desirable and such also added to cost to the consumer. It has also been expressed in the literature, that aluminum can be a health hazard when exposed to drinking water. Accordingly, if hot water from a water heater containing an aluminum alloy anode is often utilized as drinking water, for example in admixture with instant coffee etc., it could create a health hazard in long term. Powered anodes is said to be a preferred solution to the use of aluminum anodes. Another solution is to treat the water with chlorine before it enters the tank, but this is an expensive solution.

SUMMARY OF THE INVENTION

It is a feature of the present invention to provide an inexpensive method to resolve the above mentioned problem of bad odors in the hard water contained in the tank of a water heater.

Another feature of the present invention is to provide a method of neutralizing odor-causing bacteria in sulphur-containing hard water contained in a water heater by using an aluminum zinc alloy having a specific composition and introducing loose zinc metal in the tank of the water heater to neutralize the odor generating bacteria in the water.

According to the above features, from a broad aspect, the present invention provides a method of neutralizing odor-causing bacteria in sulphur-containing hard water contained in a tank of a water heater. The method comprises securing an aluminum alloy sacrificial anode to the tank and extending into the hard water contained in the tank. The sacrificial anode has 4 to 5% zinc, 0.05 to 0.25% tin, 0.25% max. silicon, and total impurities of 0.15% max. with the balance being aluminum. A small quantity of zinc material is introduced in loose form into the tank. The sacrificial anode in combination with the zinc metal introduced in the tank neutralized the bacteria and prevents the formation of bad odor in the hot water According to a further broad aspect of the present invention the zinc metal is in pellet form and introduced in the tank when the tank has water contained therein.

According to a further broad aspect of the present invention the sacrificial anode is an aluminum alloy anode containing 4 to 5% zinc, 0.05 to 0.25% max. silicon, and total impurities of 0.15% max. with the balance being aluminum.

DESCRIPTION OF THE PREFERRED EMBODIMENT

A preferred embodiment of the present invention is now described with reference to the accompanying drawing in which:

FIG. 1 is a schematic diagram of tank of an electric water heater illustrating some of the elements associated therewith and the sacrificial anode is an aluminum alloy anode and one or more zinc pellet is resting on the bottom wall of the tank.

With reference to FIG. 1, there is schematically illustrated an electric water heater tank, herein a steel tank 10 having an inlet water coupling 11 connected to a domestic water supply line 12 and a dip tube 13 for admitting water under pressure in the bottom portion of the tank. The water being fed to the tank is from a source of hard underground water which produces a rotten-egg smell when not treated. Hot water is drawn from a short pipe 14 in the top portion 14' of the tank where the water is at its hottest temperature and fed to the hot water distribution conduit 15. The water within the tank is heated by resistive heating elements 16, or by a combustion chamber under the tank when the water heater is a gas water heater. Because water in the supply line 12 may contain an undesirable amount of sulphur, it produces bad odors in the water and when the water is heated, the bad odor is amplified. The sacrificial anode 17, is usually fabricated from magnesium, and protects any exposed steel of the tank from corroding. The replacement of the anode 17 with a certain aluminum alloy anode containing zinc in small quantities of about 4 to 5% and which alloy is identified by the number "420", is used in combination with zinc material introduced in the tank in loose form to neutralize these bad odors. Certain regions have so much sulphur in their water that both hot and cold water have strong rotten egg odors although heated water produces more bad odors. With the present invention these bad odors are neutralized in the hot water drawn from the water heater.

The aluminum/zinc alloy sacrificial anode "420" is certified for use in Canada and the alloy contains 4.0 to 5.0% zinc, 0.05 to 0.25% tin, 0.25% max silicon or less and total impurities of 0.15° A) maximum with the balance being aluminum. In Canada that anode is CSA approved under Code C309.

I have experimented with the use of one of more small zinc pellets 18 loosely introduced in the water within the tank to neutralize the bad odor-causing bacteria which produce the bad odors. This experimentation resulted from my observation that in a certain residential area where the water supply produce a rotten-egg smell that certain residences had drinking water which did not smell whereas in other residences the water did have the rotten-egg smell. From closer investigation I realized that this was due to the material utilized for the water conduits. Streets where the underground piping was constructed of galvanized piping seemed to have neutralized the bacteria in the water whereas in other type conduits the smelly water was present.

Accordingly, I have found from further experimentation that the use of the "420" aluminum alloy, and the small zinc pellets in combination when exposed to such bad-odor sulphur-containing hard water acted as a neutralizer to the bacteria and produced much less hydrogen than magnesium sacrificial anodes, when active.

My invention is thus simple and inexpensive and consists simply in the addition of a zinc material, herein in pellet/tablet form in the tank of the water heater in combination with a replacement sacrificial anode formed from the "420" aluminum alloy. The pellet 18 is introduced when there is water in the tank not to impact and damage the glass lining on the inner surface of the tank. The pellet is a small disk-like pellet in the order of ⅝ diameter and ¼ inch in thickness. In a 60 gallon tank only a few of these are necessary to neutralize the odor causing bacteria. Also, in the event that the bad odor resurfaces it is only necessary to introduce a few more pellets in the tank.

My invention is also a retro-fit method wherein an existing water heater can be easily modified on site by replacing the sacrificial anode with the "420" aluminum alloy anode and adding zinc pellets into the water tank and thereby neutralizing the bad odor producing bacteria, Also, aluminum alloy anodes produce half as much current as magnesium anodes and this results in lower levels of H2S (hydrogen) gas and by lowering the H2S the rotten-egg odor is decreased. Still further, the aluminum alloy "420" sacrificial anode is expected to have a life span of at least 15 years which is much greater than a magnesium sacrificial anode.

It is within the ambit of the present invention to cover any obvious modification of the preferred embodiment described herein provided such modifications fall within the scope of the appended claims.

The invention claimed is:

1. A method of neutralizing odor-causing bacteria in sulphur-containing hard water contained in a tank of a water heater, said method comprising the steps of:
   i) securing an aluminum alloy sacrificial anode to said tank and extending into the hard water contained in said tank, and wherein said sacrificial anode has 4 to 5% zinc, 0.05 to 0.25% tin, 0.25% max. silicon, and total impurities of 0.15% max. with the balance being aluminum, and
   ii) introducing in loose form a zinc metal in said tank of said water heater and thereby neutralizing bacteria and preventing the formation of bad odor in said sulphur-containing hard water contained in said tank.

2. The method according to claim 1 wherein said zinc metal is in pellet form and introduced in said tank with water contained within the tank whereby said pellet does not damage a glass lined inner surface of said tank by impact therewith.

3. The method according to claim 2 wherein said zinc pellet is a disc-like pellet having a diameter of ⅝ inch and a thickness of ¼ inch.

4. The method of claim 1 wherein said water contained in said tank is hard underground water having a hardness of at least 100 PPM.

5. The method of claim 1 wherein said aluminum alloy sacrificial anode as compared to a magnesium sacrificial anode generates at least less than half of the current generated by a magnesium anode and therefore produces at least less than half of hydrogen in said water when operational.

6. The method according to claim 2 wherein said water heater is one of a domestic and commercial water heater.

7. The method according to claim 1 wherein said method is a retro-fit method.

\* \* \* \* \*